(12) United States Patent
Augros et al.

(10) Patent No.: US 8,074,493 B2
(45) Date of Patent: Dec. 13, 2011

(54) PRE-SIGNALING MAGNETIC PLUG

(75) Inventors: Philippe Augros, Serres-Morlaas (FR); Gérald Senger, Morlaas-Berlanne (FR)

(73) Assignee: Turbomeca, Bordes (FR)

( * ) Notice: Subject to any disclaimer, the term of this patent is extended or adjusted under 35 U.S.C. 154(b) by 387 days.

(21) Appl. No.: 12/368,346

(22) Filed: Feb. 10, 2009

(65) Prior Publication Data

US 2009/0314064 A1 Dec. 24, 2009

(30) Foreign Application Priority Data

Feb. 13, 2008 (FR) ...................................... 08 50894

(51) Int. Cl.
*G01N 33/20* (2006.01)
(52) U.S. Cl. ........................ 73/61.42; 73/53.07; 324/698
(58) Field of Classification Search ................. 73/61.42; 340/631, 627
See application file for complete search history.

(56) References Cited

U.S. PATENT DOCUMENTS

| | | | | |
|---|---|---|---|---|
| 2,462,715 A * | 2/1949 | Booth | ........................ | 200/61.09 |
| 2,689,277 A * | 9/1954 | Lidmalm | .................... | 200/61.09 |
| 2,878,342 A * | 3/1959 | Arthur | ........................ | 200/61.09 |
| 3,432,750 A * | 3/1969 | Botstiber | ........................ | 324/439 |
| 3,457,504 A * | 7/1969 | Arthur et al. | .................. | 324/701 |
| 3,553,672 A * | 1/1971 | Smith | ........................ | 340/627 |
| 4,008,464 A * | 2/1977 | Hobbie | ........................ | 340/631 |
| 5,402,113 A * | 3/1995 | Naas | ........................ | 340/631 |
| 5,583,441 A * | 12/1996 | Bitts | ........................ | 324/553 |
| 6,788,212 B2 * | 9/2004 | Sato | ........................ | 340/631 |
| 7,106,075 B2 * | 9/2006 | Hu | ........................ | 324/698 |
| 2005/0212533 A1 | 9/2005 | Itomi | | |

FOREIGN PATENT DOCUMENTS

| | | |
|---|---|---|
| DE | 197 31 960 | 2/1998 |
| DE | 10 2004 003 559 | 8/2005 |
| JP | 2002-286697 | 10/2002 |

* cited by examiner

*Primary Examiner* — Hezron E Williams
*Assistant Examiner* — Mark A Shabman
(74) *Attorney, Agent, or Firm* — Oblon, Spivak, McClelland, Maier & Neustadt, L.L.P.

(57) ABSTRACT

The invention relates to a signaling magnetic plug for a liquid circuit, the plug including a first magnetic electrode and a second magnetic electrode for coming into contact with the liquid flowing in the liquid circuit when the magnetic plug is mounted so as to detect the presence of metal particles that might be contained in the liquid. According to the invention, the plug also includes a preferably non-magnetic intermediate electrode disposed between the first and second magnetic electrodes while also being designed to be in contact with the liquid flowing in the liquid circuit when the magnetic plug is mounted, whereby said plug enables the presence of such metal particles to be detected early.

16 Claims, 1 Drawing Sheet

US 8,074,493 B2

PRE-SIGNALING MAGNETIC PLUG

FIELD OF THE INVENTION

The present invention relates to the field of detecting the wear of parts, such as (by way of example and not necessarily) rotary parts disposed in an equipment (or accessory) housing or an engine housing of an airplane.

The present invention relates more particularly to the field of magnetic plugs, in particular signaling magnetic plugs.

More precisely, the invention relates to a signaling magnetic plug for placing in a liquid circuit, the plug having a first magnetic electrode and a second magnetic electrode that are insulated from each other and that are designed to be in contact with the liquid flowing in the liquid circuit when the magnetic plug is mounted, for the purpose of detecting the presence of metal particles of ferromagnetic type that might be conveyed by the liquid.

BACKGROUND OF THE INVENTION

Traditionally, such a signaling magnetic plug is mounted on a casing containing rotary parts, such as gearwheels or bearings, that are immersed in said liquid.

In known manner, the function of the liquid circuit is generally to lubricate and/or cool the rotary parts.

It happens that the rotary parts suffer wear during their lifetime, which wear may be normal, e.g. resulting from contact friction between two gearwheels, or else it may be completely abnormal, e.g. as a result of impacts or intense friction between rotary parts due to intense and abnormal vibration propagating in the casing, and resulting in particular from a rotary part breaking. Degradation of an aircraft engine can also give rise to abnormal wear of component parts of the engine.

Whatever the cause, the wear of such parts leads to particles forming that detach from the part and that are entrained by the liquid in the liquid circuit.

Insofar as the rotary parts are generally made of metal, the particles that result from the parts wearing are electrically conductive and they are generally in the form of filings. Furthermore, the parts are usually made of a metal of the ferromagnetic type, such as iron, i.e. metal that is suitable for being attracted by a magnetic element such as a magnet.

In known manner, a signaling magnetic plug serves to detect the presence of such metal particles.

To do this, the first and second magnetic electrodes attract the metal particles while the liquid is flowing, and as a result particles accumulate on one and/or the other of the magnetic electrodes and tend to form a conductive bridge interconnecting the magnetic electrodes.

Once such a conductive bridge has formed, an associated electric circuit is in a position to detect that the conductive bridge has formed, thereby leading to a signal being sent to an operator, e.g. the pilot of the aircraft.

Such a magnetic plug is placed so as to detect the presence of particles, and on receiving a signal coming from the magnetic plug, which signal can be referred to as a "plug-on" signal, the operator must comply with utilization restrictions and perform a maintenance operation in order to determine the cause for the presence of the metal particles. For example, if particles are detected in the lubricating circuit of a helicopter engine, the "plug-on" signal requires the pilot to perform a safety landing as soon as possible for a single-engined machine, or in a multi-engine application to cause the engine concerned to idle. This affects the mission and the helicopter will need to be taken out of service for quite a long time for a maintenance operation.

Furthermore, it is often found that a magnetic plug delivers a "plug-on" signal for reasons other than abnormal wear of the engine (such signals are said to be "false-positives").

This applies for example during the first two hundred hours of operation of the engine, in which period it is found that metal particles accumulate on the plug even though the rotary parts are not worn abnormally. The cause of the metal particles being present at the beginning of the lifetime of the engine is generally due to a running-in effect or to incomplete cleaning of the engine parts during manufacture of the engine. Metal particles can therefore be present in the oil circuit in the absence of abnormal wear.

This can also happen after the running-in period, where in normal operation the particles that result from normal wear of the engine accumulate on the magnetic plug and end up producing the "plug-on" signal.

Although such "plug-on" signals are not caused by abnormal operation of the engine, they are handled as though they were so caused, leading to the same consequences in terms of operations and maintenance.

Traditionally, one solution for mitigating such false-positives and for avoiding taking the helicopter out of service, is to burn away the particles that have accumulated on the plug.

A drawback is that information is lost concerning the reason for the magnetic plug generating the "plug-on" signal. In other words, the method consisting in burning off the particles makes it impossible during future a maintenance operation to verify whether the presence of the particles on the plug was due to earlier pollution or indeed to abnormal wear, and makes it impossible to identify the parts concerned by analyzing the material.

Particle counter systems are also known that serve to monitor variation in the size and number of particles, however such systems present numerous drawbacks, in particular their costs and their weight. They also present the drawback of containing electronic circuits, and it is then necessary to ensure that they are operating properly under operational conditions.

OBJECT AND BRIEF SUMMARY OF THE INVENTION

An object of the present invention is to provide a signaling magnetic plug that is simple and inexpensive, serving firstly to detect the presence of metal particles early without giving rise to an immediate restriction on utilization conditions, and secondly enabling maintenance investigation capacities to be maintained in full.

The object of the invention is achieved by the fact that the plug of the invention further includes an intermediate electrode located between the first and second magnetic electrodes, while also being designed to be in contact with the liquid flowing in the liquid circuit when the magnetic plug is mounted, whereby said plug enables the presence of such metal particles to be detected early.

Preferably, the intermediate electrode is non-magnetic.

As metal particles accumulate on the first and second magnetic electrodes, a main conductive bridge tends to form between these two electrodes.

Before the bridge is formed between the magnetic electrodes, there comes a moment where one of the buildups of particles extending towards the other magnetic electrode comes into contact with the intermediate electrode.

This causes an intermediate conductive bridge to be formed between one of the two magnetic electrodes and the intermediate electrode, before a main bridge is formed between the two magnetic electrodes.

The intermediate electrode, which is preferably selected to be non-magnetic, does not attract metal particles and therefore does not disturb the formation of the main bridge between the first and second magnetic electrodes.

The formation of the intermediate conductive bridge enables an intermediate signal to be generated that is distinct and advantageously earlier than the signal that is generated by the main bridge forming, thereby enabling the presence of metal particles in the liquid to be detected early.

Generating such an intermediate signal, also known as pre-signaling, makes it possible to detect the presence of metal particles early and makes it possible to plan the associated maintenance and monitoring operations.

Analyzing particles associated with this intermediate detection makes it possible to determine the origin of the accumulating particles earlier and gives rise either to the plug being cleaned or else to degradation of an element of the engine being prevented.

With an aircraft, such as helicopter, the above-mentioned pre-signaling is preferably activated only when the aircraft is on the ground in order to avoid any immediate operational limitation. As a result of pre-signaling, the particles that have accumulated in this way will be analyzed a posteriori in order to determine whether or not the "plug-on" signaling is a false-positive, and if it is not a false-positive, then degradation of the engine can be prevented. The invention thus makes it possible to avoid operational limitations due to false-positives without modifying the detection performance of the magnetic electrodes.

Advantageously, the first and second magnetic electrodes are separated from each other by an insulating portion, and the intermediate electrode is disposed at least in part in the insulating portion so that it is not in contact with either of the first and second magnetic electrodes.

The intermediate electrode is thus preferably separated from the first and second magnetic electrodes by two layers of insulation.

In a first advantageous embodiment of the invention, the intermediate electrode is disposed around the periphery of the insulating portion.

Preferably, the insulating portion is generally in the shape of a cylinder sandwiched axially between the first and second electrodes, and the intermediate electrode is in the form of a ring placed on the insulating portion at distance from both the first and the second magnetic electrodes.

For example, the intermediate electrode may be placed at a predetermined distance that is closer to the first magnetic electrode than to the second magnetic electrode so as to calibrate a pre-signaling threshold.

In a second advantageous embodiment of the invention, the first and second magnetic electrodes and the intermediate electrode are in the form of bars projecting from the insulating portion.

Thus, the distal ends of the electrodes are designed to be immersed in the liquid flowing in the oil circuit.

In accordance with the invention, the material constituting the insulating portion is preferably non-magnetic.

Advantageously, the first and second magnetic electrodes, and the intermediate electrode have electrical terminals that are isolated from one another and that are designed to be connected to an electric circuit.

In the first embodiment, the terminals advantageously extend in the longitudinal direction of the magnetic plug, and they may be coaxial.

The electric circuit is arranged so as to generate a mains detection signal and also a pre-signal in accordance with the present invention.

Preferably, the liquid circuit is an oil circuit.

The invention also provides aircraft equipment provided with at least one magnetic plug of the invention.

Finally, the invention provides an aircraft engine including an oil circuit fitted with a magnetic plug of the invention.

BRIEF DESCRIPTION OF THE DRAWING

The invention can be better understood and its advantages appear better on reading the following description of embodiments given as non-limiting examples. The description refers to the accompanying drawing, in which.

MORE DETAILED DESCRIPTION

The magnetic plugs that are described below are intended, by way of example and non-exclusively, for mounting on a casing of a helicopter turbine engine 9. The magnetic plug may also be mounted on any other equipment 8 or casing including a liquid circuit, e.g. an oil circuit.

Figure 1:
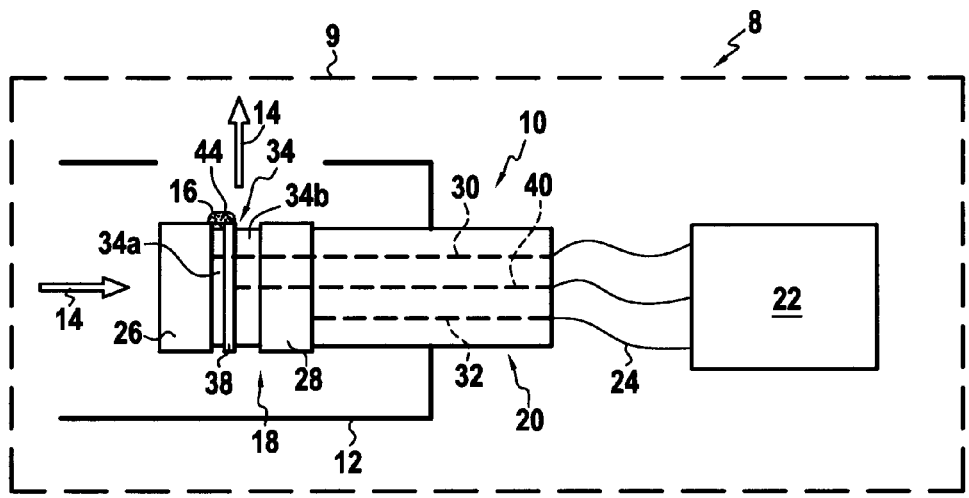
FIG. 1 is a diagrammatic view of an element of a liquid circuit having mounted thereon a magnetic plug constituting a first embodiment of the invention, an intermediate bridge of particles being formed between the first magnetic electrode and the intermediate embodiment.
Figure 2:
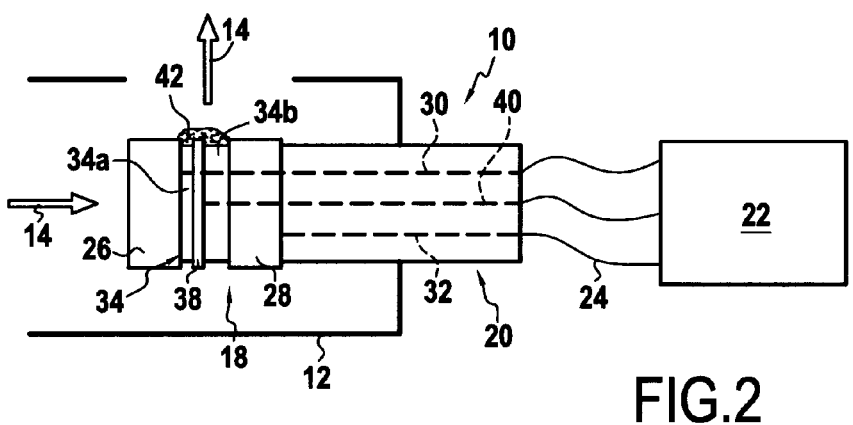
FIG. 2 shows the element of FIG. 1 where a main bridge of particles has formed between the first and second magnetic electrodes.

With reference to FIGS. 1 and 2, the description begins of a first embodiment of a signaling magnetic plug 10 of the invention.

The magnetic plug 10 is mounted on a casing 12 of a turbine engine (not shown). The casing 12 contains rotary parts constituting the turbine engine: in particular gears, bearings, and shafts enabling the rotors to be driven in rotation.

The rotary elements are immersed in a liquid circuit, specifically an oil circuit, and its flow direction is represented by arrows 14.

As explained above, the oil circuit is likely to convey metal particles 16 of the ferromagnetic type, in particular particles generated by wear of the rotary parts.

The magnetic plug 10 of the first embodiment of the invention comprises a first portion 18 that extends towards the inside of the casing 12, being immersed in the liquid circuit 14, and a second portion 20, opposite from the first, that extends to the outside of the casing 12.

Naturally, the magnetic plug 10 ensures sealing between the inside and the outside of the casing so that no oil leaks out past the magnetic plug 10. In practice, the magnetic plug 10 may include a thread enabling it to be screwed into the casing 12.

As can be seen in FIGS. 1 and 2, the magnetic plug 10, when mounted, is connected to an electric circuit 22 by electric cables 24 that emerge from the second portion 20 of the magnetic plug 10.

The function of the electric circuit 22 is to signal the presence of a bridge of conductive particles 16 in the oil circuit 14. To do this, it is possible to use any appropriate type of signaling component.

The magnetic plug 10 has a first magnetic electrode 26, specifically located at the end of the magnetic plug 10 that is remote from the second portion 20, and a second magnetic electrode 28 that lies between the first magnetic electrode 26 and the second portion 20.

As can be understood with the help of FIGS. 1 and 2, when the magnetic plug is mounted, the first and second magnetic electrodes 26 and 28 are in contact with the oil flowing in the oil circuit.

In the example described, and relative to the flow direction of the oil, the first magnetic electrode 26 is located upstream from the second magnetic electrode 28.

The term "magnetic electrode" is used to mean an electrical conductor that is also suitable for attracting metal particles.

Each of the first and second magnetic electrodes 26 and 28 has an electrical terminal that is isolated from the other, these terminals being given respective references 30 and 32, and being housed inside the magnetic plug 10 while extending in its longitudinal direction from the first portion 18 towards the second portion 20 so as to be capable of being connected to the cables 24.

Furthermore, the first and second magnetic electrodes 26 and 28 are electrically insulated from each other.

Preferably, the first and second electrodes 26 and 28 are separated from each other, preferably in the longitudinal direction of the magnetic plug 10, by an insulating portion 34, which is preferably non-magnetic.

In accordance with the present invention, the signaling magnetic plug further includes an intermediate electrode 38 that is disposed between the first and second magnetic electrodes 26 and 28, while also being designed to come into contact with the oil flowing in the oil circuit 14.

More precisely, the intermediate electrode 38 is preferably located in part in the insulating portion 34, preferably around its periphery, so as not to be in electrical contact with the first and second magnetic electrodes 26 and 28.

The intermediate electrode 38 is thus separated from the first magnetic electrode 26 by a first layer of insulation 34a and from the second magnetic electrode 28 by a second layer of insulation 34b.

Specifically, the intermediate electrode 38 forms a ring having its outer peripheral surface in contact with the oil when the plug 10 is mounted.

In manner similar to the magnetic electrodes 26 and 28, the preferably non-magnetic intermediate electrode 36 has an electrical terminal 40 similar to the terminals 30 and 32 of the magnetic electrodes, which terminal is isolated from the other terminals and is designed to be connected to the electric circuit 22 via a cable 24.

In operation, the metal particles 16 likely to be conveyed by the oil stream become fastened, by magnetism, preferably on the first magnetic electrode given its upstream position relative to the oil stream.

A main bridge 42 thus tends to form between the first and second magnetic electrodes 26 and 28. Once it has formed, the main bridge electrically interconnects the first and second magnetic electrodes 26 and 28, as shown in FIG. 2, and as a result of which the electric circuit 22 generates a signal that indicates the presence of metal particles in the oil circuit.

Prior to formation of the main bridge 42, there comes a moment, as shown in FIG. 1, where the mass of metal particles extending from the first magnetic electrode comes into contact with the intermediate electrode 38, whereby a conductive intermediate bridge 44 is formed between the first magnetic electrode 26 and the intermediate electrode 38. This causes a pre-signal to be generated by the electric circuit 22.

As can be seen in the figures, the intermediate electrode 38 preferably presents an axial width that is significantly smaller than the width of the first and second magnetic electrodes, such that the formation of the intermediate bridge 44 does not disturb the formation of the main bridge 42 between the first and second magnetic electrodes.

Furthermore, the fact that the intermediate electrode 38 is preferably non-magnetic also avoids excessively disturbing the formation of the main bridge 42.

Figure 3:
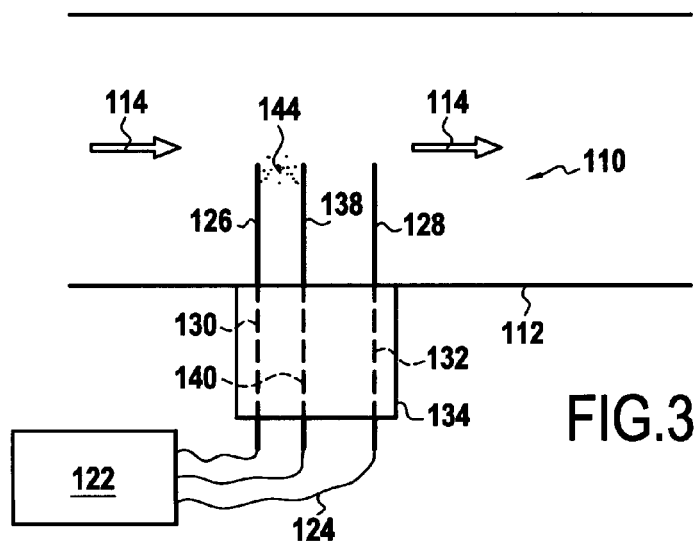
FIG. 3 is a diagram of a liquid circuit element having mounted thereon a magnetic plug constituting a second embodiment of the invention, an intermediate bridge being formed between the first magnetic electrode and the intermediate electrode.

With reference to FIG. 3, there follows a description of a second embodiment of a magnetic plug 110 of the invention.

Members that are similar to those of the first embodiment are given the same numerical references plus one hundred.

The magnetic plug 110 of FIG. 3 also has first and second magnetic electrodes 126 and 128 that are separated from each other while being designed to come into contact with the oil flowing in the oil circuit 114.

In accordance with the invention, the magnetic plug 110 also includes an intermediate electrode 138 located between the first and second magnetic electrodes 126 and 128, while likewise being designed to come into contact with the oil when the magnetic plug 110 is mounted, e.g. on a casing 112.

In the embodiment shown in FIG. 3, the first and second magnetic electrodes 126 and 128, and also the intermediate electrode 138, are in the form of bars or rods that extend from an insulating portion 134 towards the inside of the casing 112.

Each of the magnetic and intermediate electrodes is connected to an electric circuit 122 via cables 124, which cables are connected to terminals 130, 132, and 140 that are similar to those described for the first embodiment.

As can be seen in FIG. 3, relative to the flow direction of the oil, the first magnetic electrode 126 is located upstream from the second magnetic electrode 128, which second electrode is situated downstream from the intermediate electrode 138.

FIG. 3 also shows an intermediate bridge 144 of metal particles formed between the first magnetic electrode 126 and the intermediate electrode 138. This leads to the electric circuit 122 generating a pre-signal.

In similar manner to the first embodiment, a main bridge can be formed between the first magnetic electrode 126 and the second magnetic electrode 128, causing the electric circuit 122 to generate a signal.

What is claimed is:

1. A signaling magnetic plug for placing in a liquid circuit, the plug comprising:
    a first magnetic electrode and a second magnetic electrode that are insulated from each other and that are designed to be in contact with the liquid flowing in the liquid circuit when the magnetic plug is mounted, for the purpose of detecting the presence of metal particles of ferromagnetic type that might be conveyed by the liquid, when a main conductive bridge is formed between the two magnetic electrodes; and
    a non-magnetic intermediate electrode located between the first and second magnetic electrodes, while also being designed to be in contact with the liquid flowing in the liquid circuit when the magnetic plug is mounted, whereby said plug enables the presence of such metal particles to be detected when an intermediate conductive bridge is formed between one of the two magnetic electrodes and the intermediate electrode, before the main bridge is formed.

2. A magnetic plug according to claim 1, wherein the first and second magnetic electrodes are separated from each other by an insulating portion, and wherein the intermediate electrode is disposed at least in part in the insulating portion so that it is not in contact with either of the first and second magnetic electrodes.

3. A magnetic plug according to claim 2, wherein the intermediate electrode is disposed around the periphery of the insulating portion.

4. A magnetic plug according to claim 2, wherein the first and second magnetic electrodes and the intermediate electrode are in the form of bars projecting from the insulating portion.

5. A magnetic plug according to claim 2, wherein the material constituting the insulating portion is non-magnetic.

6. A magnetic plug according to claim 1, wherein the first and second magnetic electrodes, and the intermediate electrode, have electrical terminals that are isolated from one another and that are designed to be connected to an electric circuit.

7. A magnetic plug according to claim 1, wherein the liquid circuit is an oil circuit.

8. Aircraft equipment provided with at least one magnetic plug according to claim 1.

9. An aircraft engine including an oil circuit fitted with a magnetic plug according to claim 1.

10. A magnetic plug according to claim 1, wherein an axial width between the first magnetic electrode and the non-magnetic intermediate electrode is less than an axial width between the first magnetic electrode and the second magnetic electrode.

11. A magnetic plug according to claim 1, wherein the first magnetic electrode is disposed upstream of the non-magnetic intermediate electrode along a longitudinal direction of the plug and the non-magnetic intermediate electrode is disposed upstream of the second magnetic electrode in the longitudinal direction of the plug.

12. A magnetic plug for placing in a liquid circuit, the plug comprising:

a first magnetic electrode and a second magnetic electrode that are insulated from each other and that are designed to be in contact with the liquid flowing in the liquid circuit when the magnetic plug is mounted, for the purpose of detecting the presence of metal particles of ferromagnetic type that might be conveyed by the liquid, when a main conductive bridge is formed between the two magnetic electrodes; and a non-magnetic intermediate electrode located between the first and second magnetic electrodes, while also being designed to be in contact with the liquid flowing in the liquid circuit when the magnetic plug is mounted, whereby said plug enables the presence of such metal particles to be detected when an intermediate conductive bridge is formed between one of the two magnetic electrodes and the intermediate electrode, before the main bridge is formed, wherein the first and second magnetic electrodes are separated from each other by an insulating portion, and wherein the intermediate electrode is disposed at least in part in the insulating portion so that it is not in contact with either of the first and second magnetic electrodes, and the first and second magnetic electrodes and the intermediate electrode, have electrical terminals that are isolated from one another and that are designed to be connected to an electric circuit.

13. A magnetic plug according to claim 12, wherein the intermediate electrode is disposed around the periphery of the insulating portion.

14. A magnetic plug according to claim 12, wherein the first and second magnetic electrodes and the intermediate electrode are in the form of bars projecting from the insulting portion.

15. A magnetic plug according to claim 12, wherein the material constituting the insulating portion is non-magnetic.

16. A magnetic plug according to claim 12, wherein the liquid circuit is an oil circuit.

* * * * *